US00PP08486P

United States Patent [19]

Bubani

[11] Patent Number: Plant 8,486

[45] Date of Patent: Dec. 7, 1993

[54] PINTA NECTARINE TREE

[75] Inventor: Giovanni B. Bubani, 921 N. Peach Ave., Apt. #119, Fresno, Calif. 93727-2892

[73] Assignee: Giovanni B. Bubani, Fresno, Calif.

[21] Appl. No.: 958,804

[22] Filed: Oct. 9, 1992

[51] Int. Cl.[5] ..... A01H 5/00

[52] U.S. Cl. ..... Plt./41.3

[58] Field of Search ..... Plt./41.3

*Primary Examiner*—James R. Feyrer

*Attorney, Agent, or Firm*—Worrel & Worrel

[57] ABSTRACT

A new and distinct variety of nectarine tree which is somewhat remotely similar to the "Red Jim" nectarine tree (U.S. Plant Pat. No. 4,518), but from which it is distinguished by producing freestone fruit which are mature for harvesting and shipment approximately five weeks after the fruit produced by the "Red Jim" nectarine tree and which are brighter in color, of better quality and of significantly richer flavor.

1 Drawing Sheet

BACKGROUND OF THE NEW VARIETY

The present invention relates to a new and distinct variety of nectarine tree which will hereinafter be denominated varietally as the "Pinta" nectarine tree and, more particularly to a nectarine tree which produces fruit which are mature for harvesting and shipment approximately September 14 to September 28 in the San Joaquin Valley of central California, and which further is distinguished by producing large freestone fruit, the flesh of which is firm, and with a dark red skin coloration.

The development of new varieties of fruit trees for the commercial production of tree fruit is fraught with a complex interplay of considerations. While the production or discovery of new varieties is not necessarily difficult, the selection of those having commercial potential from among all of the new varieties so produced is an entirely different matter. The selection process requires painstaking observation over many years of growth during which such considerations as hardiness, resistance to disease and to pests, climate tolerance and the like may be monitored.

More significantly, for varieties to be selected for the commercial production of tree fruit, such considerations relative to the tree fruit thereof as ripening date, size, uniformity, coloration, flavor, shipping and storage attributes and the like must be evaluated. From among a plethora of candidates, only a few may warrant continued observation leading ultimately perhaps to the selection of one or two for commercial production. Of prime importance in this regard is the ripening date as it relates to the respective ripening dates of existing commercial varieties. Any new varieties which can fill a gap in the seasonal production of tree fruit, or which ripen early or late in the season so as effectively to extend the season, particularly if they otherwise possess superior attributes, are perhaps of the most potential value. The new variety of the present invention is such a variety, as will hereinafter become more clearly apparent.

ORIGIN AND ASEXUAL REPRODUCTION OF THE NEW VARIETY

The variety of nectarine tree of the present invention was discovered by the applicant in his orchard on Goodfellow Avenue, designated "Ranch No. 11," which is located near Sanger in the central San Joaquin Valley of California. The applicant discovered the new variety in 1982 as an open pollinated seedling of the "Larry's" nectarine tree (unpatented).

Asexual reproduction of the new variety was achieved by the applicant in October, 1982 by bud grafting several trees in the same orchard to the new variety. Through the growing seasons thereafter, the applicant has observed the asexually reproduced trees of the new variety and confirmed that they possess precisely the same characteristics as those of the parent seedling and as will hereinafter be described in their full pomological details.

SUMMARY OF THE NEW VARIETY

The "Pinta" nectarine tree is characterized as to novelty by producing a freestone fruit very late in the growing season which are large in size and have a dark red skin coloration. The fruit produced by the "Pinta" nectarine tree is ripe for commercial harvesting and shipment approximately September 14 to September 28 in the San Joaquin Valley of central California. The new variety is perhaps most closely similar to the "Red Jim" nectarine tree (U.S. Plant Pat. No. 4,518), but is clearly distinguishable therefrom by producing fruit which are ripe for harvesting and shipment approximately five weeks after the "Red Jim" nectarine tree. As compared with the fruit of the "Red Jim" nectarine tree, the fruit of the new variety has improved quality, substantially richer flavor and may bear more heavily due to the more vigorous growth of the trees of the new variety.

BRIEF DESCRIPTION OF THE DRAWING

The drawing is a color photograph of mature fruit of the new variety including a first so positioned as to show the apex end portion thereof, a second shown in side elevation; a third so positioned as to show the base end portion thereof; a fourth disposed in side elevation showing the suture thereof; and a fifth sectioned and laid open to show the stone in position in one of the sections and to expose the pit well of the other of the sections; and representative foliage of the new variety.

DETAILED DESCRIPTION

Referring more specifically to the pomological details of this new and distinct variety of nectarine tree, the following has been observed under the ecological conditions prevailing at the orchard of origin which is located near Sanger, Calif. All major color code designations are by reference to the *Dictionary of Color*, by Maerz and Paul, Second Edition, 1950. Common color names are also occasionally employed.

TREE

Generally: Hardy.

*Form.*—Upright to upright-spreading. Tree training system will modify somewhat the eventual tree form and density.

*Productivity.*—Very productive.

*Regularity of bearing.*—Regular under typical central San Joaquin Valley climatic conditions.

Trunk:

*Size.*—Average in diameter.

*Surface texture.*—Average in comparision with other common commercial nectarine varieties.

*Bark.*—An average amount of scarfskin is present.

*Color.*—Medium brown (7-C-10) with some greyish tones.

*Lenticels — Numbers.*—Many lenticels are present. The lenticel openings are heavily calloused with a light brown (14-F-11) colored callous tissue.

*Lenticles — size.*—Large.

Branches:

*Surface texture.*—Young branches are nearly smooth, becoming more roughened with age.

*Color — one year or older wood.*—Medium Kaffa brown (7-E-9).

*Color — current season's shoots.*—Light green (19-J-6). The surfaces of young shoots exposed to direct sunlight are tinged with red (6-J-9).

*Surface texture — immature growth.*—Nearly glabrous and very smooth.

LEAVES

Size:

*Generally.*—Large. Measurements obtained from large vigorous leaves growing near midpoint on vertical, vigorous current season's growth.

*Average length.*—19.7 cm (7.76 inches) including the petiole.

*Average width.*—4.4 cm (1.73 inches).

Form: Linear lanceolate with an acuminate leaf tip. The leaf tip is curved downwards and usually moderately twisted to one side.

Color:

*Upwardly disposed surface.*—Dark green (23-L-6).

*Downwardly disposed surface.*—Light green (22-J-6).

*Leaf vein.*—Midvein on under side is a light green-yellow (20-J-4).

Marginal form:

*Generally.*—Crenate with large, broad crenations.

*Leaf margin.*—Usually moderately undulate. At times, the margins are doubly crenate, especially at mid-margin. Most crenations are tipped with a brown trichome.

Petiole:

*Size.*—Medium.

*Length.*—Ranging from 7 mm (0.276 inches) to 11 mm (0.433 inches).

*Thickness.*—Averages 1.5 mm (0.59 inches) to 2.0 mm (0.079 inches).

*Color.*—Light green (19-K-6).

Stem glands:

*Form.*—Reniform.

*Number.*—Usually two to five glands are present.

*Position.*—Most frequently two moderately large glands are present in alternate position on the very base of the leaf margin where the lower margin is attached to the petiole groove. One to three additional smaller glands can be present further up along the lower leaf margin.

*Color.*—Bright, shiny green (19-L-5) when young, darkening substantially with age.

Stipules: Early deciduous and can only be found on new growth.

*Number.*—Two stipules are usually present, one on each side of the petiole.

*Length.*—Medium. 6 mm (0.236 inches) to 8 mm (0.315 inches (with serrate margins.

*Color.*—Light green (19-K-6) when young, darkening with age.

FLOWERS

Bloom quantity: Abundant. Most commonly 2 flower buds are present per node.

Flower buds:

*Size.*—Medium.

*Form.*—Conic.

Bud scales: Highly pubescent. Covered with a moderately long, grey pubescence.

*Color.*—Medium brown (6-I-11).

Flowers:

*Generally.*—Large and showy in form.

*Size — Generally.*—Average 38.5 mm (1.516 inches) when fully opened.

Date of full bloom: Mar. 1 in 1991. The bloom timing is considered average to slightly early in relation to other common commercial nectarine cultivars.

Petal:

*Number.*—Five.

*Color.*—Light pink (1-C-1), darker pink (1-G-2) basally and on the petal claw.

*Form.*—Generally ovate.

*Length.*—Long, averaging 20.5 mm (0.807 inches).

*Width.*—14.5 mm (0.571 inches).

*Petal claw.*—Medium in length, moderately wide and truncate.

*Margins.*—Moderately undulate, especially apically.

*Apex.*—Generally rounded.

Pedicel:

*Generally.*—Glabrous.

*Color.*—Bright green (Viridine 17-L-7).

*Length.*—Short, averaging 2.0 mm (0.0787 inches).

*Thickness.*—Averages 1.5 mm (0.059 inches).

Nectarines:

*Color.*—Bright orange (10-K-11).

Anthers:

*Size.*—Medium.

*Color.*—Tan (9-H-3) ventrally and red (Ember 5-K-10) coloration on the anther margins and dorsally.

Pollen: Abundant.

*Color.*—Yellow (10-L-3).

Stamens:

*Filament color.*—White to very light pink (1-B-1) when the flower is young, darkening to a pale violet (Bridal Rose 3-F-3) when fully mature.

*Length.*—14 mm (0.551 inches) to 15 mm (0.591 inches). Stamens are equal to slightly longer in length than the pistil at full maturity.

Pistil: Glabrous.

*Color.*—Light green (17-I-3).

*Length.*—16.5 mm (0.6496 inches) including the ovary.

FRUIT

Maturity when described: Ripe for commercial harvesting and shipment approximately September 14 to September 28 near Sanger in the central San Joaquin Valley of California.

Size:

*Generally.*—Uniform, large.

*Average diameter in the axial plane.*—76 mm (2.99 inches).

*Average diameter transverse in the suture plane.*—69 mm (2.72 inches).

*Average cheek diameter.*—76 mm (2.99 inches).

Form:

*Uniformity.*—Generally ovate in lateral aspect, although some variability is present. The fruit is generally oval to globose in axial aspect. The compressed portion of the oval is usually on the suture surfaces, both dorsal and ventral, rather than laterally.

Suture:

*Generally.*—A distinct but very shallow groove from apex to base. Usually the suture has no distinct coloration of its own, but takes on the coloration of the blush or ground color underneath the suture. At times a few very fine red lines can be visible when the suture is underlain with yellow ground color.

Ventral surface:

*Generally.*—Rounded with only a slight amount of lipping. Usually one side is slightly more lipped than the other.

Stem cavity:

*Generally.*—Oval in form and moderately deep.

*Width.*—Averages 31 mm (1.22 inches).

*Depth.*—Ranges from 13 mm (0.512 inches) to 16 mm (0.630 inches).

*Length.*—33 mm (1.30 inches).

Fruit shoulders:

*Generally.*—Most fruit shoulders are creased by the imprint of the branch on which the fruit was borne.

Fruit base: Variable, but usually slightly truncated. Base angle can also be variable, but most often is slightly oblique to the fruit axis.

Fruit apex: Rounded in form with a very low blunt apex. Pistil point is variable, but most often is slightly oblique. A distinct depression is present on both the dorsal and the ventral sides of the apex with the ventral depression usually more distinct.

Fruit stem: Medium in length.

*Size.*—Averages 8 mm (0.315 inches to 12 mm (0.472 inches).

*Thickness.*—Average 3.0 mm (0.118 inches).

*Color.*—Light green (20-L-3).

Skins:

*Thickness.*—Medium and tenacious to flesh at commercial maturity.

*Texture.*—Glabrous, smooth and glossy.

*Flavor.*—Mild without much acidity.

*Tendency to crack.*—No tendency to crack observed.

*Blush color.*—Dark garnet red (6-L-10) in its darkest tones and ranges to a lighter red (6-K-11). The mottle overlying the blush is also often a very dark red (8-L-5). Ranges from 60 percent to 90 percent of the surface of the fruit. Blush pattern is usually washed but a substantial amount of color mottle is also present.

*Ground color.*—Bright yellow (10-K-4).

*Flesh color.*—Uniform yellow-amber (10-K-4) from under the skin inwards toward the stone cavity.

*Surface of pit cavity.*—Bright ember red (5-K-10) wtih rays of red coloration extending several millimeters into the flesh. White callous tissue is present in moderate amounts on the surface of the stone cavity.

*Flesh flavor.*—Highly flavored and well balanced.

*Aroma.*—Slight, pleasant.

*Texture.*—Firm at commercial maturity.

*Fibers — numbers.*—Few fibers of medium length are present. The fibers are light in color.

*Fibers — texture.*—Tender.

*Ripening.*—Ripens evenly.

Stone:

*Attachment.*—Full freestone.

*Fibers — numbers.*—Few.

*Fibers — length.*—Moderately short.

*Size — length.*—Average 40.2 mm (1.58 inches).

*Size — width.*—Average 26.0 mm (1.023 inches).

*Size — thickness.*—Average 19.4 mm (0.764 inches).

*Form — generally.*—Obovate.

*Apex — shape.*—Variable, from sharp and acuminate to only moderately acute.

*Color — dry.*—Golden brown (14-H-11) with darker areas which have a purplish stain. A moderate amount of white callous tissue is present usually attached to grooves or pits on the stone surface.

*Base — shape.*—Broadly truncate. Base angle slightly to moderately oblique the stone axis.

*Sides — generally.*—Usually unequal.

*Hilum.*—Medium in size, oval in form and well defined by a raised and substantially grooved collar.

*Stone — surface.*—Coarsely grooved, especially over the apical shoulders. Several large irregular pits present laterally.

*Ventral edge.*—Broad with several low wings present, converging apically. The wings are somewhat indistinct and coalesced at the basal 6 mm (0.236 inches) to 8 mm (0.315 inches) of the ventral suture.

*Dorsal edge.*—Medium in width and substantally raised. A moderately deep and wide groove is usually present, extending from the stone base to about mid-suture. The groove narrows into a line from mid-suture up to the apex. The suture is moderately eroded over the apical shoulder. The dorsal edge is cut in several places by cross grooves.

*Tendency to split.*—No tendency to split observed.

Use: This new cultivar is a late ripening, fresh market nectarine with potential for use in both local market and long distance shipping.

Although the new variety of nectarine tree possesses the described characteristics noted above as a result of the growing conditions prevailing near Sanger in the central part of the San Joaquin Valley of California, it is to be understood that variations of the usual magnitude and characteristics incident to changes in growing conditions, irrigation, fertilization, pruning and pest control are to be expected.

Having thus described and illustrated my new variety of nectarine tree, what I claim as new and desire to be secured by Plant Letters Patent is:

1. A new and distinct variety of nectarine tree substantially as illustrated and described and which is somewhat remotely similar to the "Red Jim" nectarine tree (U.S. Plant Pat. No. 4,518), but from which it is distinguished by producing freestone fruit which are mature for commercial harvesting and shipment approximately September 14 to September 28 in the San Joaquin Valley of central California and which further are of improved quality and richer flavor when compared thereto.

* * * * *

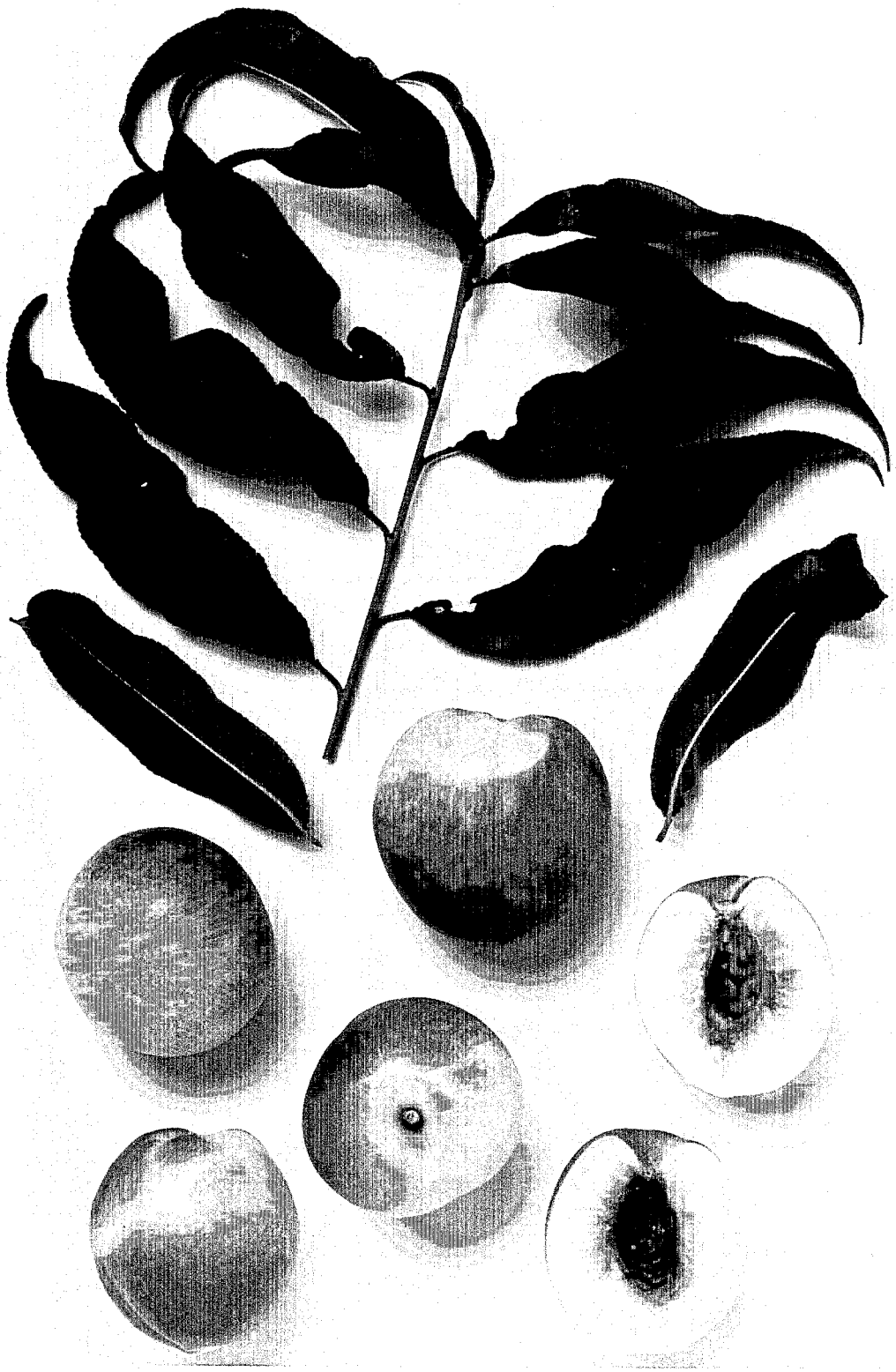

UNITED STATES PATENT AND TRADEMARK OFFICE

CERTIFICATE OF CORRECTION

PATENT NO. : Plant 8,486

DATED : December 7, 1993

INVENTOR(S) : Giovanni Bosco Bubani

It is certified that error appears in the above-indentified patent and that said Letters Patent is hereby corrected as shown below:

On the Title Page:

Item [19], delete "Bubani" and insert —Bosco Bubani—.
Item [75], delete "B." and substitute —Bosco—.
Item [73], delete "B." and substitute —Bosco—.

Column 1, line 6, delete "particularly" and substitute ---particularly,---.

Column 2, line 36, delete "thereof," and substitute ---thereof;---.

Column 4, line 16, delete "inches(" and substitute ---inches)---.

Column 5, line 47, delete "truncated" and substitute ---truncate---.

Signed and Sealed this

Twenty-first Day of June, 1994

*Attest:*

*Attesting Officer*

BRUCE LEHMAN

*Commissioner of Patents and Trademarks*